(12) United States Patent
Tritz et al.

(10) Patent No.: US 11,517,048 B2
(45) Date of Patent: Dec. 6, 2022

(54) AEROSOL-GENERATING ARTICLE, DEVICE AND SYSTEM WITH OPTIMIZED SUBSTRATE USAGE

(71) Applicant: PHILIP MORRIS PRODUCTS S.A., Neuchatel (CH)

(72) Inventors: Poh Yoke Tritz, Yverdon-les-Bains (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 364 days.

(21) Appl. No.: 16/611,506

(22) PCT Filed: May 9, 2018

(86) PCT No.: PCT/EP2018/061945
§ 371 (c)(1),
(2) Date: Nov. 7, 2019

(87) PCT Pub. No.: WO2018/206615
PCT Pub. Date: Nov. 15, 2018

(65) Prior Publication Data
US 2020/0337366 A1 Oct. 29, 2020

(30) Foreign Application Priority Data

May 10, 2017 (EP) .................................... 17170413

(51) Int. Cl.
*A24F 13/00* (2006.01)
*A24F 17/00* (2006.01)
(Continued)

(52) U.S. Cl.
CPC ............ *A24F 40/46* (2020.01); *A24B 15/167* (2016.11); *A24D 1/20* (2020.01); *A61M 15/06* (2013.01);
(Continued)

(58) Field of Classification Search
CPC ........ A24B 15/167; A24D 1/002; A24D 1/20; A24F 40/20; A24F 40/46; A24F 40/465;
(Continued)

(56) References Cited

U.S. PATENT DOCUMENTS 725,671 A 4/1903 Butler
4,574,821 A * 3/1986 Fischer .................... A24D 1/00
131/365
(Continued)

FOREIGN PATENT DOCUMENTS

CN 105307526 2/2016
EP 1338546 9/1963
(Continued)

OTHER PUBLICATIONS

PCT Search Report and Written Opinion for PCT/EP2018/061945 dated Oct. 25, 2018 (28 pages).
(Continued)

*Primary Examiner* — Abdullah A Riyami
*Assistant Examiner* — Thang H Nguyen
(74) *Attorney, Agent, or Firm* — Mueting Raasch Group

(57) ABSTRACT

The present invention relates to a rod-shaped aerosol-generating article for use with an electrically heated aerosol-generating device. The article comprises a substrate core and a filler sleeve surrounding the substrate core. The substrate core comprises an aerosol-forming substrate and has a non-circular outer cross-section. The invention further relates to electrically heated aerosol-generating device and an aerosol-generating system for use with an aerosol-generating article.

10 Claims, 4 Drawing Sheets

Figure 1:
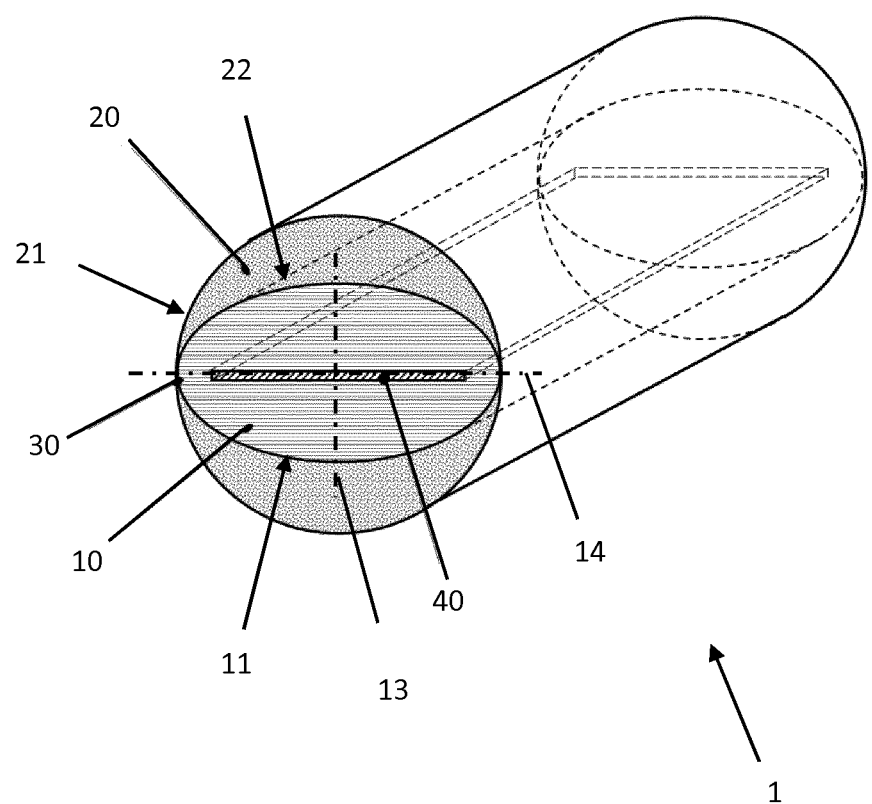

(51) Int. Cl.
   *A24F 25/00*    (2006.01)
   *A24F 40/46*    (2020.01)
   *A24B 15/167*   (2020.01)
   *A61M 15/06*    (2006.01)
   *A24D 1/20*     (2020.01)
   *A61M 11/04*    (2006.01)
   *A24F 40/465*   (2020.01)
   *A24D 1/00*     (2020.01)
   *A24F 40/20*    (2020.01)

(52) U.S. Cl.
   CPC .............. *A24D 1/002* (2013.01); *A24F 40/20* (2020.01); *A24F 40/465* (2020.01); *A61M 11/042* (2014.02); *H05B 2203/021* (2013.01)

(58) Field of Classification Search
   CPC ................ A61M 11/042; A61M 15/06; H05B 2203/021
   See application file for complete search history.

(56) References Cited

U.S. PATENT DOCUMENTS

| | | | | |
|---|---|---|---|---|
| 5,065,776 A * | 11/1991 | Lawson | ............... | A24D 1/02 131/194 |
| 5,105,838 A * | 4/1992 | White | .................. | A24D 1/00 131/194 |
| 5,247,947 A * | 9/1993 | Clearman | ............ | A24D 1/22 131/194 |
| 5,271,419 A * | 12/1993 | Arzonico | ............ | A24D 3/043 131/365 |
| 5,415,186 A * | 5/1995 | Casey, III | .......... | A24B 15/287 131/365 |
| 9,516,899 B2 | 12/2016 | Plojoux | | |
| 9,717,277 B2 * | 8/2017 | Mironov | ............ | A24F 40/465 |
| 10,561,174 B2 * | 2/2020 | Prestia | ................ | A24C 5/40 |
| 10,821,240 B2 * | 11/2020 | McCullough | ........ | H05B 1/025 |
| 2011/0290269 A1 * | 12/2011 | Shimizu | ............... | A24F 40/46 131/330 |
| 2014/0305448 A1 | 10/2014 | Zuber | | |
| 2015/0223515 A1 | 8/2015 | McCullough | | |
| 2016/0354561 A1 * | 12/2016 | McCullough | ........... | A24C 5/01 |
| 2017/0055580 A1 * | 3/2017 | Blandino | ............... | H05B 6/36 |
| 2017/0119050 A1 | 5/2017 | Blandino | | |

FOREIGN PATENT DOCUMENTS

| | | |
|---|---|---|
| EP | 0156628 | 10/1985 |
| EP | 0202835 | 11/1986 |
| EP | 2394520 | 12/2011 |
| EP | 2967155 | 1/2016 |
| EP | 2967156 | 1/2016 |
| GB | 2260887 | 5/1993 |
| GB | 2534215 | 7/2016 |
| JP | H09-173041 | 7/1997 |
| JP | H11-164679 | 6/1999 |
| JP | 2015-506170 | 3/2015 |
| KZ | 31520 | 9/2016 |
| RU | 2602969 | 11/2016 |
| WO | WO 2014/087529 | 6/2014 |
| WO | WO 2015/165814 | 11/2015 |
| WO | WO 2016/023174 | 2/2016 |
| WO | WO 2016/174179 | 11/2016 |
| WO | WO 2016/184929 | 11/2016 |
| WO | WO 20160184930 | 11/2016 |

OTHER PUBLICATIONS

International Preliminary Report on Patentability for PCT/EP2018/061945 dated Aug. 30, 2019, 2019 (11 pages).
Office Action issued in Russia for Application No. 2019140279 dated Sep. 10, 2021 (17 pages). English translation included.
Office Action issued in China for Application No. 201880019874.8 dated Apr. 21, 2022 (20 pages). English translation included.
Office Action issued in Japan for Application No. 2019-561809 dated Jun. 13, 2022 (10 pages). English translation included.

* cited by examiner

AEROSOL-GENERATING ARTICLE, DEVICE AND SYSTEM WITH OPTIMIZED SUBSTRATE USAGE

This application is a U.S. National Stage Application of International Application No. PCT/EP2018/061945 filed May 9, 2018, which was published in English on Nov. 15, 2018 as International Publication No. WO 2018/206615 A1. International Application No. PCT/EP2018/061945 claims priority to European Application No. 17170413.3 filed May 10, 2017.

The present invention relates to an aerosol-generating article in the form of a rod comprising an aerosol-forming substrate to be heated. The invention further relates to an electrically heated aerosol-generating device for use with such an article as well as to an aerosol-generating system comprising such an article and such a device.

Rod-shaped aerosol-generating articles comprising an aerosol-forming substrate to form an inhalable aerosol upon heating are generally known. For heating the substrate, the article may be inserted into a receiving chamber of an aerosol-generating device that includes an electrical heater. The heater may be a resistive heater or an inductive heater. In both cases, the heater may comprise a strip-shaped heating element that is either part of the device or integrated in the aerosol-generating article, thus being part of the latter. For example, in case of a resistive heater, the heating element may be an electrically resistive heating blade arranged with the device and configured to penetrate an internal portion of the article upon inserting the article into the device. Likewise, in case of an inductive heater, the heating element may be a metallic susceptor tape arranged with the substrate of an aerosol-generating article.

Although such heating elements have proven advantageous with regard to a simple and inexpensive manufacturing, it has been observed that the substrate within the article is only partially heated when the heating element is strip-shaped. In particular, it has been observed that only portions in close proximity to the strip-shaped heating element are sufficiently heated such as to allow for aerosol formation.

Therefore, it would be desirable to have an aerosol-generating article, an electrically heated aerosol-generating device and an aerosol-generating system with the advantages of prior art solutions but without their limitations. In particular, it would be desirable to have an aerosol-generating article, device and system providing an optimized usage of the aerosol-forming substrate.

According to a first aspect of the invention there is provided an aerosol-generating article in the form of a rod that is configured for use in an aerosol-generating device. The article comprises a substrate core having a non-circular outer cross-section including an aerosol-forming substrate to be heated. Furthermore, the article comprises a filler sleeve surrounding the substrate core.

As used herein, the term 'aerosol-generating article' refers to an article comprising an aerosol-forming substrate that, when heated, releases volatile compounds that can form an aerosol. Preferably, the aerosol-generating article is a heated aerosol-generating article. That is, an aerosol-generating article which comprises an aerosol-forming substrate that is intended to be heated rather than combusted in order to release volatile compounds that can form an aerosol. The aerosol-generating article may be a consumable, in particular a consumable to be discarded after a single use. The rod-shaped article may be an article, in particular a tobacco article, resembling conventional cigarettes.

As used herein, the term 'aerosol-forming substrate' denotes a substrate formed from or comprising an aerosol-forming material that is capable of releasing volatile compounds upon heating for generating an aerosol. The aerosol-forming substrate may contain a tobacco material or may contain a non-tobacco material or a combination of both, tobacco material and non-tobacco material. The aerosol-forming substrate may be cellulose material impregnated with nicotine, preferably comprising one or more flavours. Advantageously, the aerosol-forming substrate comprises tobacco material, preferable homogenised tobacco material, preferably comprising one or more aerosol-formers. As used herein, the term 'homogenised tobacco material' denotes a material formed by agglomerating particulate tobacco. The aerosol-forming substrate may, for example, be in the form of a crimped and gathered sheet of tobacco material. The aerosol-forming substrate may also be in the form of cut or shredded homogenised tobacco material arranged into a rod shape. The aerosol-forming substrate may further comprise an aerosol former. Examples of suitable aerosol formers are glycerine and propylene glycol. The aerosol-forming substrate may also comprise other additives and ingredients, such as nicotine or flavourants. In particular, the aerosol-forming substrate may include water, solvents, ethanol, plant extracts and natural or artificial flavours. The aerosol-forming substrate may also be a paste-like material, a sachet of porous material comprising aerosol-forming substrate, or, for example, loose tobacco mixed with a gelling agent or sticky agent, which could include a common aerosol former such as glycerine, and then is compressed or molded into a plug.

As used herein, the term 'aerosol-generating device' is used to describe a device that interacts with an aerosol-forming substrate of an aerosol-generating article for generating an aerosol. Preferably, the aerosol-generating device is a puffing device that interacts with an aerosol-forming substrate of an aerosol-generating article to generate an aerosol that is directly inhalable by a user thorough the user's mouth.

According to the invention, it has been recognized that when using strip-shaped heating elements heat transfer inside the aerosol-forming substrate of a rod-shaped aerosol-generating article—as seen in the cross-sectional view of the article—essentially follows the cross-sectional profile of the strip-shaped heating element extending through the substrate. Accordingly, while heating of the substrate is typically sufficient in close proximity to the heating element, the heating efficiency decreases with increasing distance to the heating element. As a consequence, for up to 30 percent to 40 percent of the aerosol-forming substrate within currently available rod-shaped articles aerosol formation is insufficient.

To remedy this deficiency, the present inventions suggests to confine the aerosol-forming substrate within the article to a restricted volume of appropriate shape which is chosen such as to be sufficiently heatable by a strip-shaped heating element to still allow for aerosol formation. Accordingly, the present invention provides a rod-shaped aerosol-generating article which comprises a substrate containing core having an outer cross-section that is adapted shape-wise to the effective cross-sectional heating area of strip-shaped heating elements. According to the invention, it has been recognized that the effective cross-sectional heating area of a strip-shaped heating element is non-circular. Therefore, the aerosol-generating article according to the invention comprises a substrate core having a non-circular outer cross-section which comprises the aerosol-forming substrate to be heated.

As a result, the aerosol-generating article according to the invention may advantageously comprise up to 30 percent to 40 percent less aerosol-forming substrate as compared to standard rod-shaped articles currently existing in the market. However, as compared to standard articles, the aerosol-generating article according to the invention still provides essentially the same performance in terms of aerosol formation. The latter advantage is due to the fact that the aerosol-generating article according to the invention—as compared to currently available rod-shaped articles—indeed comprises less aerosol-forming substrate in total, but the same effective amount of substrate heatable by the strip-shaped heating element.

In particular, the effective cross-sectional heating area of a strip-shaped heating element may be oblate or oblong. Moreover, the outer profile of cross-sectional heating area may be at least partially curved. For example, the effective cross-sectional heating area may be oval, in particular elliptical. Likewise, the effective cross-sectional heating area may be essentially rectangular, in particular rectangular with rounded corners. Accordingly, the outer cross-section of the substrate core may be oblong or oblate. Preferably, the outer cross-section of the substrate core may be oval, in particular elliptical, or rectangular, in particular rectangular with rounded corners.

Moreover, the non-circular outer cross-section of the substrate core may comprise at least one axis of symmetry. In particular, the non-circular outer cross-section of the substrate core may comprise a major axis of symmetry and a minor axis of symmetry being orthogonal to each other.

As used herein, the term 'outer cross-section' and 'inner cross-section' refer to the outer and inner counter line or profile of a respective element as seen in a cross-sectional view through the geometric element normal to a length extension of the element.

To replace the saved substrate volume, the aerosol-generating article according to the invention comprises a filler sleeve surrounding the substrate core. Preferably, the outer cross-section of the filler sleeve matches or corresponds to the inner cross-section of a receiving chamber of an aerosol-generating device the article is to be used with. By this, the article according to the invention may be securely received in the receiving chamber, in particular as secure as compared to currently available rod-shaped articles having essentially the same outer cross-section as the filler sleeve.

Preferably, a length extension of the filler sleeve is equal to the length extension of the substrate core. Of course, the length extension of the filler sleeve may be also larger or smaller than the length extension of the substrate core.

When used herein in relation to the substrate core and the filler sleeve, the term 'length extension' refers to the longitudinal or axial direction of the rod-shaped article or the filler sleeve, respectively. Likewise, the term 'radially' refers to the transverse direction of the rod-shaped article or the filler sleeve, respectively.

Depending on the shape of the inner cross-section of the receiving chamber the article is to be at least partially accommodated in, the filler sleeve may have an oval or elliptical or circular or square or rectangular or triangular or polygonal outer cross-section. Preferably, the filler sleeve has a circular outer cross-section.

As regards the interface between the filler sleeve and the substrate core, the filler sleeve may surround the substrate core such that the inner circumferential surface of the sleeve is at least partially arranged at a radial distance to the outer circumferential surface of the substrate core. Accordingly, the aerosol-generating article may comprise a gap volume between the inner cross-section of the sleeve and the outer cross-section of the substrate core. The gap volume may extend at least partially along at least one of the length extension or the circumference of the substrate core. Advantageously, the gap volume may serve as air flow passage on the outer circumferential surface of the substrate core, thus, allowing volatile compounds that are released from the aerosol-forming substrate upon heating to freely escape from the article. Even more advantageously, the size and shape of the gap volume may be chosen such as to provide an aerosol-forming article having a pre-defined resistance to draw. In general, the overall design of the article may be chosen such as to provide an aerosol-forming article having a pre-defined resistance to draw. For example, the material, material densities and geometry of the filler sleeve and the substrate may be chosen such as to provide a pre-defined resistance to draw.

The filler sleeve, in particular an inner circumferential surface of the filler sleeve, may be at least partially in contact with an outer circumferential surface of the substrate core. This proves advantageous with regard to the dimensional stability of the aerosol-generating article. In case the inner circumferential surface of the filler is only partially in contact with the outer circumferential surface of the substrate core, the article may comprise an air flow passage between the substrate core and the filler sleeve as described above.

In the latter case but also in case the inner circumferential surface of the filler sleeve is not in direct contact with the outer circumferential surface of the substrate core, the inner cross-section of the filler sleeve may have a different shape as compared to the non-circular outer cross-section of the substrate core.

Alternatively, the inner circumferential surface of the filler sleeve may be entirely in contact with the outer circumferential surface of the substrate core. In particular, the filler sleeve may surround the substrate core in a tight fitting manner. This further enhances the dimensional stability of the aerosol-generating article. In this case, the filler sleeve may have a non-circular inner cross-section corresponding to the non-circular outer cross-section of the substrate core.

The filler sleeve may be attached to the substrate core either irremovably or removably. As used herein, the term 'irremovably attached' refers to a firm bond between the filler sleeve and the substrate core. For example, the filler sleeve may be glued to or firmly pressed or tightly fitted around the substrate core. In contrast, the term 'removably attached' as used herein refers to a detachable connection of the filler sleeve to the substrate core. In the latter case, the filler sleeve advantageously allows for multiple use. Accordingly, after consumption of the aerosol-forming substrate in the substrate core, the filler sleeve may be extracted from the used-up substrate core and re-attached with another substrate core comprising fresh aerosol-forming substrate.

The filler sleeve advantageously comprises a heat resistant filler material that is heat resistant at least up to those temperatures enabling aerosol formation, that is, up to at least 150 degree Celsius, in particular up to at least 250 degree Celsius, preferably up to at least 300 degree Celsius, even more preferably up to at least 400 degree Celsius. For example, the heat resistant filler material may include at least one of a ceramic material or a heat resistant plastic material, such as polyether ether ketone (PEEK) or a polyimide.

As used herein, the term "heat resistant material" refers to a material which substantially does not undergo a phase transition to a liquid or gaseous phase, in particular does not melt or volatilize, or does not burn below the temperature up to which it is defined to be heat resistant. This definition also refers to any insert sleeves defined further below.

The filler sleeve may comprise a porous filler material, for example a porous ceramic material. A porous material advantageously allows for storing at least one volatile substance in the filler sleeve which can be activated and released from the filler sleeve upon heating.

Accordingly, the filler sleeve may comprise at least one of a flavor agent, an aroma agent, an anti-odor agent, or a chemical-trapping agent, such as activated charcoal. Preferably, the flavor agent is conditioned to be perceived in at least one of a user's mouth or a user's lung, whereas the aroma agent is conditioned to be perceived in a user's nose, but preferably not in the user's mouth and lung.

Preferably, the filler is free of tobacco material, that is, does not comprise any tobacco material.

The at least one volatile substance in the filler sleeve can be activated and released upon being heated. Preferably, the volatile substance is conditioned such as to require less thermal energy than the aerosol-forming substrate in the substrate core. Due to this, the volatile substance in the filler sleeve advantageously is heated together with the aerosol-forming substrate in the substrate core or released in a timed relation with the aerosol-forming substrate. In particular, a single heating element may be used for this. The single heating preferably is the heating element that is to be brought into contact with the aerosol-forming substrate in the substrate core.

The substrate core may comprise a wrapper surrounding the aerosol-forming substrate. Primarily, the wrapper serves to keep the aerosol-forming substrate together and to maintain the desired non-circular cross-sectional shape of the substrate core. For example, the wrapper may be a paper wrapper, in particular a paper wrapper made of cigarette paper. Alternatively, the wrapper may be a foil, for example made of metal or plastics. Preferably, the wrapper is fluid permeable such as to allow vaporized aerosol-forming substrate to be released from the substrate core. The wrapper may be porous. Furthermore, the wrapper may comprise at least one volatile substance to be activated and released from the wrapper upon heating. For example, the wrapper may be impregnated with a flavoring volatile substance.

In case the aerosol-generating article is to be used with an aerosol-generating device that comprises a strip-shaped heating element as integral part of the device, the article may comprise a preformed strip-shaped slot for receiving the strip-shaped heating element. Likewise, the heating element may be integral part of the aerosol-generating article. That is, the aerosol-generating article may comprise a strip-shaped heating element extending at least partially through the substrate core.

In both cases, the non-circular outer cross-section of the substrate core advantageously is such that the shortest distance of any point of the outer cross-sectional counter line of the substrate core to the strip-shaped slot or to the strip-shaped heating element, respectively, is in a range of 0.2 millimeters to 4 millimeters, in particular in a range of 0.3 millimeters to 3 millimeters, preferably, in the range of 0.5 millimeters and 2 millimeters.

Moreover, in case the non-circular outer cross-section of the substrate core comprises a major axis of symmetry and a minor axis of symmetry being orthogonal to each other, the strip-shaped slot preferably extends at least partially through the substrate core such that a width extension of the slot essentially coincides with the major axis of symmetry and a thickness extension of the slot essentially coincides with the minor axis of symmetry. Accordingly, a length extension of the slot essentially coincides with the longitudinal center axis of the substrate core and the rod-shaped article, respectively. Likewise, the strip-shaped heating element may extend at least partially through the substrate core such that a width extension and a thickness extension of the heating element essentially coincide with a major axis of symmetry and a minor axis of symmetry of the non-circular outer cross-section of the substrate core, respectively. Accordingly, a length extension of the heating element coincides with the longitudinal center axis of the substrate core and the rod-shaped article, respectively.

As used herein, the terms 'width extension' and 'thickness extension' denote a width extension and a thickness extension of a respective element—as referred to herein—which both extend through a center of mass or a geometric center of the element. Accordingly, having a width extension and a thickness extension of a respective element—as referred to herein—to essentially coincide with a major axis of symmetry and a minor axis of symmetry preferably implies that the major axis of symmetry and the minor axis of symmetry extend through a center of mass or a geometric center of the element.

The term 'essentially coincide' also includes off-axis deviations of up to 20 degrees, in particular up to 10 degrees from a coinciding on-axis orientation. Preferably, the above described width and thickness extensions coincide with a major axis of symmetry or a minor axis of symmetry of the non-circular outer cross-section of the substrate core, respectively.

In both cases, the non-circular outer cross-section of the substrate core thus essentially matches the effective cross-sectional heating area of a strip-shaped heating element. Furthermore, having the slot fixedly arranged with regard to the outer cross-section of the substrate core also ensures that a user of the device will assemble the aerosol-generating article and the aerosol-generating device in the same well-defined way. This assures that there is little or essentially no variability of the orientation of the substrate core relative to the heating element. This in turn reduces the variability of the product performance. This proves to be even more advantageous in case the aerosol-forming substrate is structured along a predefined direction as seen in the cross-sectional view of the article. This may be the case for example, if the aerosol-generating article comprises crimped tobacco cast leaf as aerosol-forming substrate arranged in layers.

As used herein, the term 'strip-shaped' refers to an element which has a length extension and a width extension which are both larger than a thickness extension of the element. Preferably, the length extension is also larger than the width extension. Accordingly, the strip-shaped heating element may be an elongated strip-shaped heating element. Likewise, the strip-shaped slot may be an elongated strip-shaped slot. However, the length extension of the strip-shaped heating element or the strip-shaped slot may be equal to the respective width extension. In particular, the strip-shaped heating element may be a blade, a plate, a sheet, a band, or a foil.

When inserted or arranged in the substrate core, the strip-shaped heating element is located in thermal contact or close thermal proximity with the aerosol-forming substrate. This allows the substrate to be efficiently heated aerosol formation. Preferably, the heating is in direct physical contact with the aerosol-forming substrate.

As described above, electrically heating of the aerosol-forming substrate within the aerosol-generating article may be based either on resistive heating or inductive heating.

Accordingly, the strip-shaped heating element may be a resistive heating element. For heat generation, the resistive heating element preferably comprises an electrically resistive material configured to heat up when an electrical current is passed there through. Advantageously, the electrically resistive material is a material having a defined relationship between temperature and resistivity. In particular, this allows for temperature measurement and temperature control. Preferably, the electrically resistive material is a metal, such as platinum or stainless steel.

For example, the resistive heating element may comprise an insulating substrate in the form of a blade having a metal track formed thereon which heats up when passing an electrical current through the track. The insulating substrate may be a metal blade coated with an insulating ceramic material. Likewise, the resistive heating element may be a flat U- or V-shaped metal blade. The legs of the U- or V-shaped metal blade provide respective connectors for supplying an electrical current.

Furthermore, the resistive heating element preferably is configured to get automatically coupled with a power supply of the aerosol-generating device upon inserting the aerosol-generating article into a receiving chamber of the aerosol-generating device.

Alternatively, the strip-shaped heating element may be a susceptor element to interact with an alternating electromagnetic field generated by an induction source of the aerosol-generating device. As used herein, the term 'susceptor element' refers to an element comprising a material that is capable to convert electromagnetic energy into heat. Thus, when located in an alternating electromagnetic field, the susceptor element is heated. This may be the result of at least one of hysteresis losses or eddy currents induced in the susceptor element, depending on the electrical and magnetic properties of the susceptor material. For example, the susceptor element may comprise aluminum, or a ferrous or ferrite material such as a stainless steel or a ferrite ceramic.

Apart from the aerosol-forming substrate, the aerosol-generating article may further comprise at least one of a support element, an aerosol-cooling element, a filter element and a mouthpiece element. Any one or any combination of these elements may be arranged sequentially to the substrate core. These elements may have the same outer cross-section as the substrate core. In particular, the substrate core and any one or any combination of the above elements may be arranged sequentially and circumscribed by an outer wrapper to form a core rod. This core rod may be surrounded by the filler sleeve at least partially along its length extension. Alternatively, the aforementioned elements may have the same outer cross-section as the filler sleeve. In this case, the filler sleeve may only surround the substrate core.

According to the first aspect of the invention there is also provided an aerosol-generating system comprising an aerosol-generating article according to the first aspect of the invention and as described before. The system further comprises an electrically heated aerosol-generating device for use with the aerosol-generating article. The aerosol-generating device comprises a receiving chamber for at least partially accommodating the aerosol-generating article in the receiving chamber.

Preferably, the receiving chamber has an inner cross-section corresponding to the outer cross-section of the filler sleeve of the aerosol-generating article. Advantageously, this facilitates inserting and securely holding the aerosol-generating article in the receiving chamber. Furthermore, this ensures that a user of the device will assemble the aerosol-generating article and the aerosol-generating device in the same well-defined way. This in turn assures that there is little or essentially no variability of the orientation of the substrate core relative to the heating element which reduces the variability of the product performance.

The electrically heated aerosol-generating device may either comprise a resistive heater or an inductive heater. Accordingly, the heater preferably comprises a strip-shaped resistive heating element or strip-shaped inductive heating element, in particular strip-shaped susceptor element, as described above. In both cases, the heating element may be either part of the device, in particular at least partially arranged within the receiving chamber such as to penetrate an internal portion of the article upon inserting it into the device. Alternatively, the heating element may be integrated in the aerosol-generating article, thus being part thereof. Further features and advantages of a respective resistive or inductive heating element, in particular a susceptor element, have been described above with regard to the aerosol-generating article of the first aspect of this invention. Therefore, these features and advantages will therefore not be repeated.

The aerosol-generating device may comprise a power supply for supplying power to the respective heater as well as an electric circuitry for controlling the heating process.

In case of a resistive heater, the resistive heating element may be operatively coupled with the power supply via the circuitry. Thus, upon passing an electrical current there through the resistive heating element heats up due to Joule heating. Furthermore, when having the resistive heating element integrated in the aerosol-generating article, the aerosol-generating device may comprise a docking connector. The docking connector is configured for operatively coupling the heating element with the power supply upon insertion of the article into the receiving chamber of the device.

In case of an inductive heater, the aerosol-generating device may comprise an induction source. The induction source is operatively coupled to the power supply and the electric circuitry for generating an alternating electromagnetic field. The induction source preferably comprises an alternating current generator that is operatively coupled to an induction coil which generates the alternating electromagnetic field upon passing an alternating current there through. The alternating electromagnetic field in turn induces at least one of eddy currents or hysteresis losses in the susceptor element, depending on its electrical and magnetic properties.

Further features and advantages of aerosol-generating system according to the first aspect of invention have been described above with regard to the aerosol-generating article having a non-circular substrate core and a surrounding filler sleeve and also with regard to the above described features of an aerosol-generating device that is to interact with such an article. Therefore, these features and advantages will not be repeated.

According to a second aspect of the invention there is also provided an electrically heated aerosol-generating device for use with an aerosol-generating article. The aerosol-generating article has a non-circular outer cross-section including an aerosol-forming substrate to be heated by a strip-shaped heating element. The device comprises an insert sleeve forming a receiving chamber within the sleeve for at least partially accommodating the aerosol-generating article in the receiving chamber. The insert sleeve has a non-circular inner cross-section. Furthermore, the insert sleeve is removably arranged within a cavity of the aerosol-generating device. Due to this, the insert sleeve advantageously serves as an adapter enabling the cavity of the aerosol-generating device to interact with an aerosol-generating article having a corresponding non-circular outer cross-section. That is to interact with an aerosol-generating article that is configured for optimized usage of the aerosol-forming substrate when heated by a strip-shaped heating element.

Advantageously, the non-circular inner cross-section of the insert sleeve is oblong or oblate. Preferably, the inner cross-section of the insert sleeve is oval, in particular elliptical, or rectangular, in particular rectangular with rounded corners.

In case the outer cross-section of the aerosol-generating article to be used with the device comprises a major axis of symmetry and a minor axis of symmetry, the non-circular inner cross-section of the insert sleeve advantageously also comprises a corresponding major axis of symmetry and a corresponding minor axis of symmetry.

Preferably, the strip-shaped heating element to be used for heating the substrate within the non-circular cross-sectional profile of the article is part of the aerosol-generating device. Accordingly, the aerosol-generating device may comprise a strip-shaped heating element for insertion into the aerosol-generating article upon receiving the article in the device. In particular, the strip-shaped heating element is arranged within the cavity of the device, preferably symmetrically along a center axis of the cavity.

The aerosol-generating article may be inserted into the receiving chamber of the insert sleeve prior to inserting the latter into the cavity of the aerosol-generating device. Alternatively, the insert sleeve may be inserted into the cavity of the device prior to inserting the article into the receiving chamber of the insert sleeve.

The heating element may be removably arranged within the cavity of the aerosol-generating device. This proves advantageous for cleaning and replacing the heating element. In addition, this facilitates inserting the strip-shaped heating element into the substrate of the aerosol-generating article.

The article preferably comprises strip-shaped slot for receiving the strip-shaped heating element. This also facilitates inserting the strip-shaped heating element into the substrate of the aerosol-generating article. Advantageously, the strip-shaped slot extends at least partially through the substrate of the article such that a width extension and a thickness extension of the slot essentially coincide respectively with a major axis of symmetry and a minor axis of symmetry of the non-circular cross-sectional profile of the article, if present.

The non-circular inner cross-section of the insert sleeve advantageously is such that the shortest distance of any point of the inner cross-sectional counter line of the insert sleeve to the strip-shaped heating element is in a range of 0.2 millimeters to 4 millimeters, in particular in a range of 0.3 millimeters to 3 millimeters, preferably, in the range of 0.5 millimeters and 2 millimeters.

In case the inner cross-section of the insert sleeve comprises a major axis of symmetry and a minor axis of symmetry, the strip-shaped heating element is arranged at least partially within the receiving chamber of the insert sleeve such that a width extension of the strip-shaped heating element essentially coincides with the major axis of symmetry and a thickness extension of the heating element essentially coincides with the minor axis of symmetry. Furthermore, having the heating element fixedly arranged with regard to the inner cross-section of the receiving chamber also ensures there is little or essentially no variability of the orientation of the heating element relative to the outer cross-section of the article upon inserting into the receiving chamber. This in turn reduces the variability of the product performance.

Preferably, the insert sleeve comprises a heat resistant material that is heat resistant at least up to those temperatures enabling aerosol formation, that is, up to at least 150 degree Celsius, in particular up to at least 250 degree Celsius, preferably up to at least 300 degree Celsius, even more preferably up to at least 400 degree Celsius. For example, the heat resistant material may include at least one of a ceramic material or a heat resistant plastic material, such as polyether ether ketone (PEEK) or a polyimide.

Further features and advantages of the aerosol-generating device according to the second aspect of invention have been already described above with regard to the first aspect of the invention and will therefore not be repeated.

According to a third aspect of the invention there is also provided an electrically heated aerosol-generating device for use with an aerosol-generating article. The aerosol-generating article has a non-circular outer cross-section including an aerosol-forming substrate to be heated by a strip-shaped heating element. The device comprises a receiving chamber for at least partially accommodating the aerosol-generating article. The receiving chamber has a non-circular inner cross-section. Preferably the non-circular inner cross-section corresponds to the non-circular outer cross-section of the article to be used with the device. Advantageously, the non-circular inner cross-section of the receiving chamber is oblong or oblate. Preferably, the inner cross-section of the receiving chamber is oval, in particular elliptical, or rectangular, in particular rectangular with rounded corners. Moreover, the non-circular inner cross-section of the receiving chamber may comprise a major axis of symmetry and a minor axis of symmetry. Due to the non-circular inner cross-section of the receiving chamber the aerosol-generating device according to the third aspect of the invention is readily prepared for interaction with an aerosol-generating article having a corresponding non-circular outer cross-section. This in turn is preferred as described above with regard to the first and second aspect of the invention.

The device according to the third aspect of the invention further comprises a strip-shaped heating element for insertion into the aerosol-generating article when being received in the receiving chamber. In particular, the strip-shaped heating element is arranged within the receiving chamber of the device, preferably symmetrically along a center axis of the receiving chamber.

The non-circular inner cross-section of the receiving chamber advantageously is such that the shortest distance of any point of the inner cross-sectional counter line of the receiving chamber to the strip-shaped heating element is in a range of 0.2 millimeters to 4 millimeters, in particular in a range of 0.3 millimeters to 3 millimeters, preferably, in the range of 0.5 millimeters and 2 millimeters.

In case the non-circular inner cross-section of the receiving chamber comprises a major axis of symmetry and a minor axis of symmetry, the strip-shaped heating element preferably is arranged at least partially within the receiving chamber such that a width extension of the heating element essentially coincides with the major axis of symmetry and a thickness extension of the heating element essentially coincides with the minor axis of symmetry. Due to this arrangement the aerosol-generating device advantageously enables the heating element to engage with the aerosol-generating article in the same well-defined way. This ensures that the outer cross-section of the aerosol-generating article automatically matches to the effective cross-sectional heating area of a strip-shaped heating element. Accordingly, this assures that there is little or essentially no variability of the orientation of the heating element relative to the outer cross-section of the article. Advantageously, this reduces the variability of the product performance.

The heating element may be removably arranged at least partially within the receiving chamber. This proves advantageous for cleaning and replacing the heating element. In addition, this facilitates inserting the strip-shaped heating element into the substrate of the aerosol-generating article prior to inserting the aerosol-generating article into the receiving chamber of the device.

Advantageously, the receiving chamber is formed by an insert sleeve having a corresponding non-circular inner cross-section. The insert sleeve is configured to be removably arranged within a cavity of the aerosol-generating device. Accordingly, the removable insert sleeve serves as adapter as described above.

Preferably, the insert sleeve comprises a heat resistant material that is heat resistant at least up to those temperatures enabling aerosol formation, that is, up to at least 150 degree Celsius, in particular up to at least 250 degree Celsius, preferably up to at least 300 degree Celsius, even more preferably up to at least 400 degree Celsius. For example, the heat resistant material may include at least one of a ceramic material or a heat resistant plastic material, such as polyether ether ketone (PEEK) or a polyimide.

Further features and advantages of aerosol-generating device according to the third aspect of invention have been already described above with regard to the first and second aspect of the invention. Therefore, these features and advantages will not be repeated.

According to the invention there is also provided an aerosol-generating system comprising an electrically heated aerosol-generating device according to the second or third aspect of the invention and as described above. The system further comprises an aerosol-generating article in the form of a rod for use with the aerosol-generating device. The aerosol-generating article has a non-circular outer cross-section corresponding to the non-circular inner cross-section of the receiving chamber of the device. Furthermore, the aerosol-generating article comprises an aerosol-forming substrate within its non-circular outer cross-section.

Further features and advantages of the aerosol-generating system according to this aspect of the invention have been already described with regard to aerosol-generating devices and aerosol-generating articles according to the second and third aspect of the invention. Therefore, these features and advantages will not be repeated.

Figure 2:
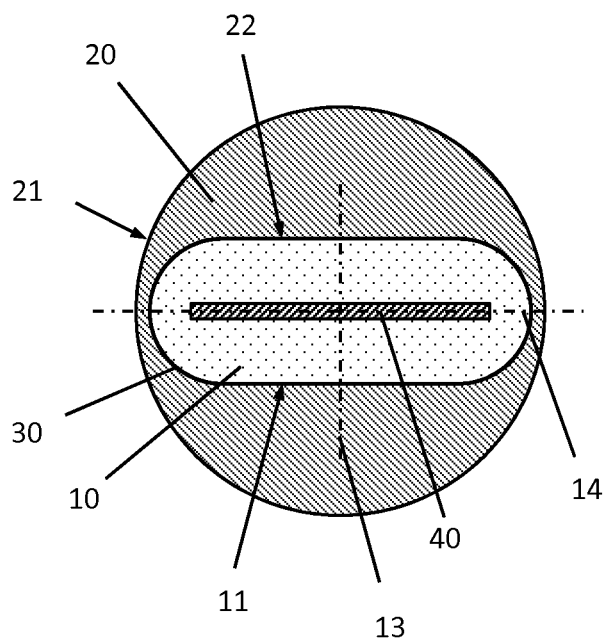
Figure 3:
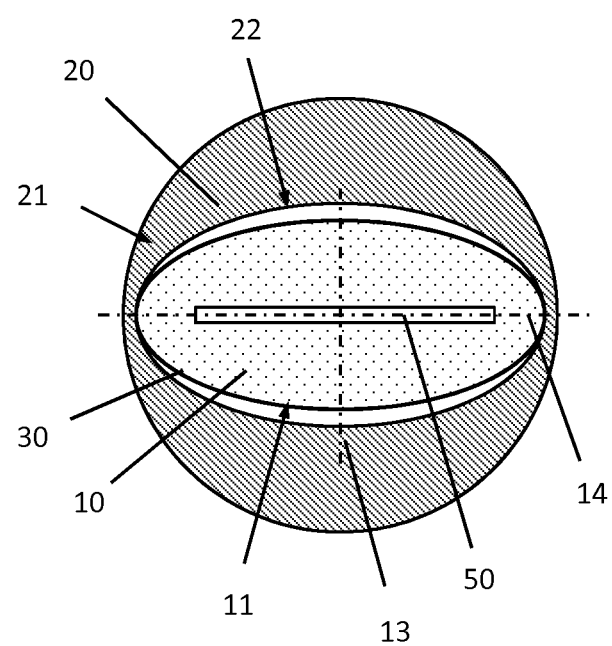
Figure 4:
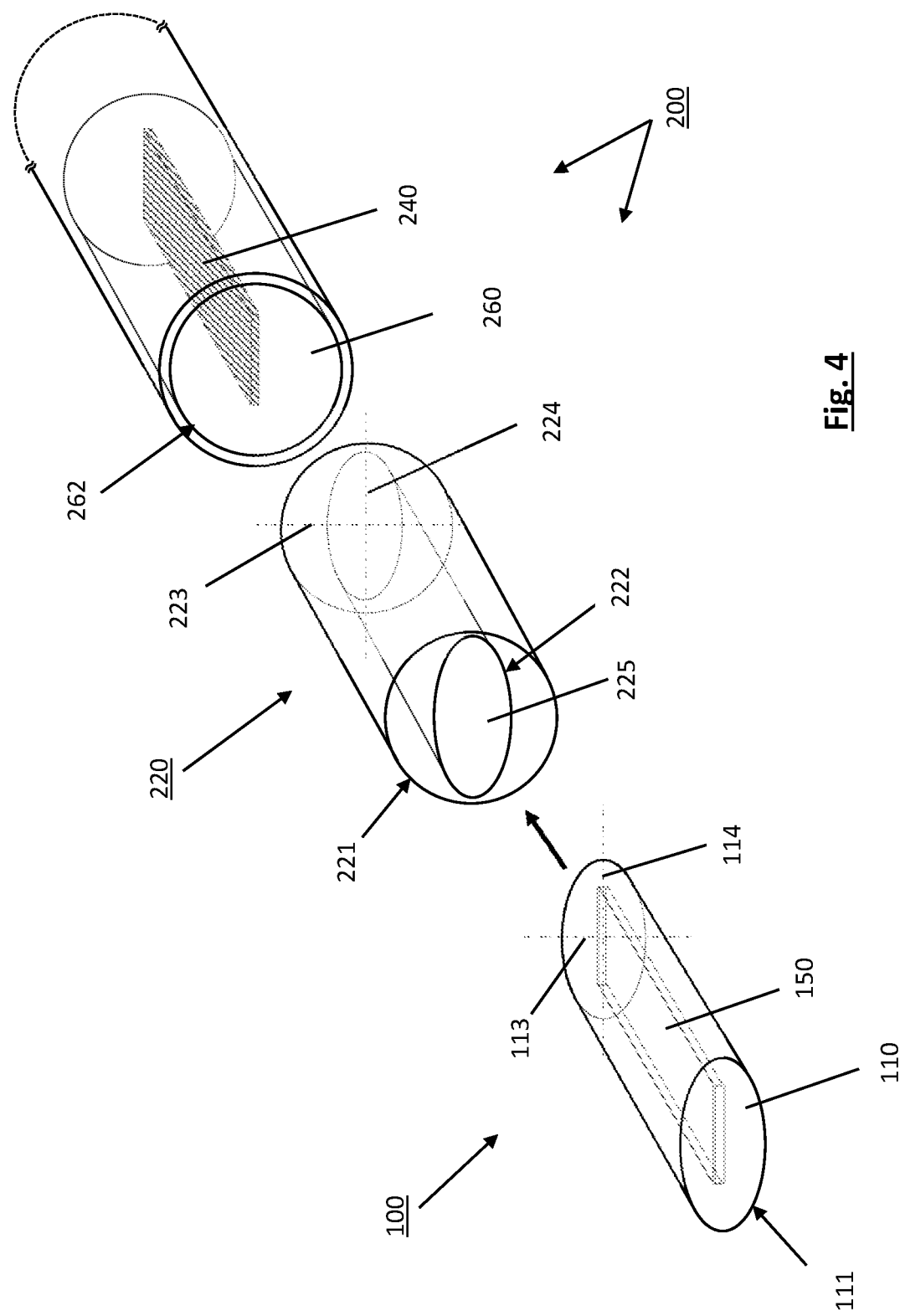
Figure 5:
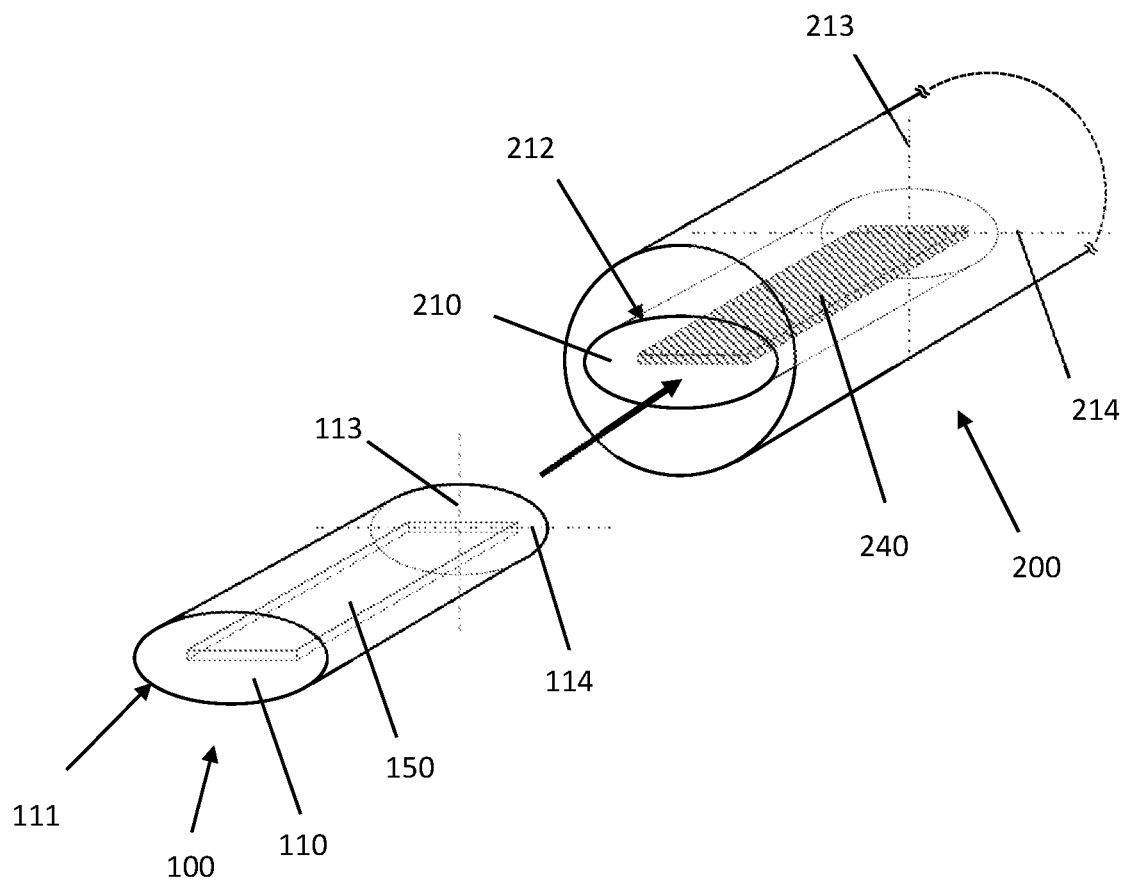

The invention will be further described, by way of examples only, with reference to the accompanying drawings, in which:

FIG. 1 schematically illustrates a first embodiment of an aerosol-generating article according to the first aspect of the invention in a perspective view;

FIG. 2 schematically illustrates a second embodiment of an aerosol-generating article according to the first aspect of the invention in a cross-sectional view;

FIG. 3 schematically illustrates a third embodiment of an aerosol-generating article according to the first aspect of the invention in a cross-sectional view;

FIG. 4 schematically illustrates an exemplary embodiment of an aerosol-generating system according to the second aspect of the invention in a perspective view; and FIG. 5 schematically illustrates an exemplary embodiment of an aerosol-generating system according to the third aspect of the invention in a perspective view.

FIG. 1 is a schematic illustration of a first embodiment of an aerosol-generating article 1 according to the first aspect of the invention. The article 1 comprises an aerosol-forming substrate to be heated in order to release volatile compounds that can form an aerosol. The article 1 is to be inserted into a receiving chamber of an electrically driven aerosol-generating device (not shown) which comprises an electrical heater for heating the aerosol-forming substrate. In the present embodiment, the aerosol-generating article 1 is configured for inductive heating of its substrate. For this, the rod-shaped article 1 comprises a strip-shaped susceptor element 40 (as strip-shaped heating element 40) which extends through the center of the article 1 along the length extension of the article 1. For example, the susceptor element 40 may be a strip-shaped foil of aluminum. As counterpart to the strip-shaped susceptor element 40, the electrical heater of the aerosol-generating device comprises an induction source which is configured for generating an alternating electromagnetic field within the receiving chamber. Thus, upon accommodating the aerosol-generating article 1 in the receiving chamber, the susceptor element 40 heats up due to eddy currents and/or hysteresis losses that are induced by the alternating electromagnetic field in the susceptor material depending on its electrical and magnetic properties. Advantageously, the susceptor element 40 is in direct physical contact with the aerosol-forming substrate such as to allow an efficient heating of the substrate.

As described above, the heating efficiency decreases with increasing distance to the heating element. Accordingly, as seen in a cross-sectional view, the heating element provides an effective cross-sectional heating area in close proximity to the element in which heating is still sufficient for aerosol formation. Beyond this effective heating area, the thermal energy provided by the heating element typically is too low to allow for sufficient aerosol formation.

In order to optimize the usage of the aerosol-forming substrate of the article, the present invention suggests confining the substrate distribution within the aerosol-generating article to a restricted area of appropriate shape which matches the effective cross-sectional heating area of the heating element to be used as good as possible.

With regard to the strip-shaped susceptor element 40 according to the embodiment of FIG. 1, the effective cross-sectional heating area is non-circular, in particular oblate due to the oblong cross-sectional profile of the rectangular strip shape. Hence, in order to optimize the usage of substrate, the aerosol-forming substrate of the article 1 according to the embodiment of FIG. 1 is confined in a substrate core 10 whose outer cross-section 11 is non-circular such as to match the effective cross-sectional heating area of the strip-shaped susceptor element 40 as good as possible.

As can be seen from FIG. 1, the non-circular outer cross-section 11 of the substrate core 10 is oval. In particular, the outer cross-section 11 of the substrate core 10 advantageously is such that the shortest distance of any point of the outer cross-sectional counter line of the substrate core 10 to the strip-shaped susceptor element 40 is in a range of 0.5 millimeters to 2 millimeters.

As can be further seen from FIG. 1, the oval outer cross-section 11 of the substrate core 10 comprises a minor axis of symmetry 13 and a major axis of symmetry 14 which are orthogonal to each other. In order to provide a homogenous heating of the substrate within the substrate core 10, the strip-shaped susceptor element 40 advantageously extends lengthwise through the entire substrate core 10 along its center axis such that a width extension of the susceptor element 40 essentially coincides with the major axis of symmetry 14 and a thickness extension of the susceptor element 40 essentially coincides with the minor axis of symmetry 13.

The article 1 according to the embodiment of FIG. 1 further comprises a filler sleeve 20 surrounding the substrate core 10. As such, the filler sleeve 20 primarily serves as volumetric filler which defines the outer shape of the aerosol-generating article 1. In particular, the filler sleeve 20 may serve to define an outer shape of the article that is comparable to currently available rod-shaped articles. Advantageously, this allows the article 1 to be used with aerosol-generating devices already existing in the market. In the present embodiment, the filler sleeve 20 comprises a circular outer cross-section 21 causing the outer shape of the rod-shaped article 1 to be a circular cylinder.

In contrast, the inner cross-section 22 of the filler sleeve 20 is oval. In particular, the inner cross-section 22 of the filler sleeve 20 corresponds to the oval outer cross-section 11 of the substrate core 10 such the inner circumferential surface of the filler sleeve 20 is entirely in contact with the outer circumferential surface of the substrate core 10 in a tight fitting manner. Advantageously, this provides a high dimensional stability of the aerosol-generating article 1.

In the present embodiment, the filler sleeve 20 comprises a porous ceramic material as filler material. Within the porous ceramic, the filler sleeve 20 further comprises a volatile flavor agent which can be activated and released from the filler sleeve upon heating. Preferably, the volatile substance is conditioned such as to be heated together with the aerosol-forming substrate in the substrate core 10.

The aerosol-forming substrate within the substrate core 10 is surrounded by a paper wrapper 30. The paper wrapper 30 serves to keep the substrate together and thus defines the outer circumferential surface of the substrate core 10. Moreover, the paper wrapper 30 is fluid permeable such as to allow vaporized aerosol-forming substrate to be released from the substrate core 10.

FIG. 2 schematically illustrates a second embodiment of an aerosol-generating article 1 according to the first aspect of the invention. The article according to FIG. 2 is similar to the article according to FIG. 1. Therefore, identical or similar features are denoted with the same reference signs. In contrast to the article according to FIG. 1, the article 1 according to FIG. 2 comprises a substrate core whose outer cross-section is rectangular with rounded corners. Accordingly, the inner cross-section 22 of the filler sleeve 20 is also rectangular with rounded corners corresponding to the outer cross-section 11 of the substrate core 10. As compared to the FIG. 1, the outer cross-sectional outer counter line of the substrate core 10 is even closer to the outer cross-sectional counter line of the susceptor element 40. Here, the shortest distance of any point of the outer cross-sectional counter line of the substrate core 10 to the strip-shaped susceptor element 40 is in a range of 0.5 millimeters to 2 millimeters, in particular in a range of 0.5 millimeters to 1.5 millimeters. Advantageously, this allows for an even more sufficient usage of the aerosol-forming substrate within the article 1.

FIG. 3 schematically illustrates a third embodiment of an aerosol-generating article 1 according to the first aspect of the invention. The article according to FIG. 3 is similar to the article according to FIG. 1. Therefore, identical or similar features are denoted with the same reference signs. In contrast to the article according to FIG. 1, the inner circumferential surface of the filler sleeve 20 of the article 1 according to FIG. 3 is not entirely in contact with the outer circumferential surface of the substrate core 10. Though the inner cross-section 22 of the filler sleeve 20 is oval too, the semi-minor axis of the inner cross-section 22 of the filler sleeve 20 is different in length from the semi-minor axis of the outer cross-section 11 of the substrate core 10. In contrast, the semi-major axis of the inner cross-section 22 of the filler sleeve 20 is identical to the semi-major axis of the outer cross-section 11 of the substrate core 10. Due to this, the inner circumferential surface of the filler sleeve 20 is in contact with the outer circumferential surface of the substrate core 10 only at the outer ends of the semi-major axis of the substrate core 10. As a result, two gap volumes are formed between the inner cross-section 22 of the filler sleeve 11 and the outer cross-section 11 of the substrate core 10. The gap volumes axially extend along the length extension of the substrate core 10, at both sides of the substrate core 10 with regard to its major axis of symmetry. Advantageously, the gap volumes serve as air flow passages along the outer circumferential surface of the substrate core 10, allowing volatile compounds that are released from the aerosol-forming substrate to freely escape from the article 1. Even more advantageously, the size and shape of the gap volumes may be chosen such as to provide a pre-defined resistance to draw.

Further in contrast to the article according to FIG. 1, the article according to FIG. 3 does not comprise a heating element as integral part of the article. Instead, the article 1 is configured for interaction with a strip-shaped heating element that is integral part of an aerosol-generating device the article 1 is to be used with. To facilitate insertion of the heating element into the substrate of the article 1, the article 1 according to FIG. 3 comprises a preformed strip-shaped slot 50 extending lengthwise through the entire substrate core 10 along its center axis. The strip-shaped slot 50 is arranged such that a width extension of the slot 50 essentially coincides with the major axis of symmetry 14 of the substrate core 10 and a thickness extension of the slot 50 essentially coincides with the minor axis of symmetry 13 of the substrate core 10. Advantageously, this allows for a homogenous heating of the substrate within the substrate core 10. In order to achieve an optimum usage of the substrate, the outer cross-section 11 of the substrate core 10 is such that the shortest distance of any point of the outer cross-sectional counter line of the substrate core 10 to the strip-shaped slot 50 is in a range of 0.5 millimeters to 2 millimeters, in particular in a range of 0.5 millimeters to 1.5 millimeters.

FIG. 4 schematically illustrates an exemplary embodiment of an aerosol-generating system according to the second aspect of the invention. The system comprises an aerosol-generating article 100 and an electrically heated aerosol-generating device 200 for use with the article 100. The aerosol-generating article 100 has an oval outer cross-section 111 including an aerosol-forming substrate 110 to be heated by a strip-shaped heating element 240. In the present embodiment, the strip-shaped heating element 240 is integral part of the device 200. For example, the heating element 240 may be a heating blade made of stainless steel which can be heated either resistively or inductively. Alternatively, the strip-shaped heating element may be integral part of the aerosol-generating article 100. For example, the heating element may be a metallic susceptor tape arranged within the substrate 110 of the article 100 which may be heatable by an induction source of the device upon engaging the article with the device.

As can been seen from FIG. 4, the heating element 240 is arranged within a cavity 260 of the device 200 in which the article 100 is to be inserted. The cavity 260 has a circular inner cross-section, like many currently available devices which are configured to interact with rod-shaped articles having a circular outer cross-section. In order to enable the circular cavity 260 of the device 200 to interact with an article 100 having a non-circular outer cross-section, that is, with the aerosol-generating article 100 according to the second aspect of the invention, the aerosol-generating device 200 according to FIG. 4 comprises an insert sleeve 220. The outer shape of the insert sleeve 220 is configured such as to be removably arrangeable within the cavity 260 of the device 200. In contrast, the inner shape of insert sleeve 220 is such as to form a receiving chamber 225 for accommodating the aerosol-generating article 100 within the sleeve. Accordingly, the inner cross-section 222 of the insert sleeve 220 is oval corresponding to the oval outer cross-section 111 of the article 100. Likewise, the outer cross-section 221 of the insert sleeve 220 is circular corresponding to the inner cross-section 262 of the cavity 260. As a result, the insert sleeve 220 serves as an adapter between the oval article 100 and the circular cavity 260 of the device 200. Thus, the insert sleeve 220 adapts the aerosol-generating device 200—having a strip-shaped heating element 240—to be used with an aerosol-generating article 100 which comprises an aerosol-forming substrate within an oval cross-section and which therefore is optimized for use with a strip-shaped heating element 240.

Upon assembling the article 100 and the insert sleeve 220 into the cavity 260 of device 200, the strip-shaped heating element 240 is centrally arranged within the cavity 260 such that a width extension of the heating element 240 essentially coincides with a major axis 114 of symmetry of the outer cross-section 111 of the article 100 as well as with a major axis 224 of symmetry of the outer cross-section 221 of the insert sleeve 220. Likewise, a thickness extension of the heating element 240 essentially coincides with a minor axis 113 of symmetry of the outer cross-section 111 of the article 100 as well as with a minor axis 223 of symmetry of the outer cross-section 221 of the insert sleeve 220. On the one hand, this ensures an optimum usage of the substrate 110 within the article 100 when used in combination with the strip-shaped heating element 240 of the device 200. On the other hand, this also ensures a correct insertion of the article 100 into the receiving chamber 225 of the sleeve 220 and also a correct insertion of the insert sleeve 220 into the cavity 260 of the device 200.

Preferably, the inner cross-section of the insert sleeve 220 is such that upon insertion into the cavity 260 the shortest distance of any point of the inner cross-sectional counter line of the insert sleeve 220 to the strip-shaped heating element 240 is in a range of 0.5 millimeters to 2 millimeters, in particular in a range of 0.5 millimeters to 1.5 millimeters.

In order facilitate insertion of the strip-shaped heating element 240 into the substrate 110 of the article 100, the article 100 comprises a pre-formed strip-shaped slot 150 for receiving the strip-shaped heating element 240. The slot 150 symmetrically extends along a center axis of the article 100 such that a width extension of the slot 150 essentially coincides with a major axis 114 of symmetry of the oval article 100. Likewise, a thickness extension of the heating element 240 essentially coincides with a minor axis 113 of symmetry of the oval article 100.

FIG. 5 schematically illustrates an exemplary embodiment of an aerosol-generating system according to the third aspect of the invention. The system is similar to the aerosol-generating system according to the second aspect of the invention as shown in FIG. 4. Therefore, identical or similar features are denoted with the same reference signs. In contrast to the device of FIG. 4, the aerosol-generating device 200 according to FIG. 5 itself comprises a receiving chamber 210 having a non-circular, in particular oval inner cross-section 212 for accommodating an aerosol-generating article 100 that has a corresponding oval outer cross-section 111.

Within the receiving chamber 210, the device 200 comprises a strip-shaped heating element 240. The heating element 240 is integral part of the aerosol-generating device 200. For example, the heating element 240 may be a heating blade made of stainless steel which can be heated either resistively or inductively.

Advantageously, the heating element 240 is centrally arranged within the receiving chamber 210 such that a width extension of the heating element 240 essentially coincides with a major axis 214 of symmetry of the outer cross-section 212 of the receiving chamber 210. Likewise, a thickness extension of the heating element 240 essentially coincides with a minor axis 213 of symmetry of the outer cross-section 212 of the receiving chamber 210.

Preferably, the oval inner cross-section 212 of receiving chamber 210 is such that the shortest distance of any point of the inner cross-sectional counter line of the receiving chamber 210 to the strip-shaped heating element 240 is in a range of 0.5 millimeters to 2 millimeters, in particular in a range of 0.5 millimeters to 1.5 millimeters.

Moreover, the heating element 240 may be removably arranged within the receiving chamber 210. This proves advantageous for cleaning and replacing the heating element 240.

The invention claimed is:

1. A rod-shaped aerosol-generating article for use with an electrically heated aerosol-generating device, the article comprising a substrate core and a filler sleeve surrounding the substrate core, the substrate core comprising an aerosol-forming substrate and having a non-circular outer cross-section, and the filler sleeve having a circular outer cross-section and comprising a heat resistant filler material that is heat resistant up to at least 150 degree Celsius.

2. The article according to claim 1, wherein the filler sleeve is at least partially in contact with an outer circumferential surface of the substrate core.

3. The article according to claim 1, wherein the filler sleeve has a non-circular inner cross-section corresponding to the non-circular outer cross-section of the substrate core.

4. The article according to claim 1, wherein the filler sleeve is removably or irremovably attached to the substrate core.

5. The article according to claim 1, wherein the filler sleeve comprises at least one of a porous filler material, a flavor agent, an aroma agent, an anti-odor agent, a chemical-trapping agent.

6. The article according to claim 1, wherein the substrate core comprises a wrapper surrounding the aerosol-forming substrate.

7. The article according to claim 1, wherein the non-circular outer cross-section of the substrate core comprises a major axis of symmetry and a minor axis of symmetry being orthogonal to each other, and wherein the article further comprises a preformed strip-shaped slot for inserting a strip-shaped heating element, the strip-shaped slot extending at least partially through the substrate core such that a width extension of the slot essentially coincides with the major axis of symmetry and a thickness extension of the slot substantially coincides with the minor axis of symmetry.

8. The article according to claim 1, wherein the non-circular outer cross-section of the substrate core comprises a major axis of symmetry and a minor axis of symmetry being orthogonal to each other, and wherein the article further comprises a strip-shaped heating element extending at least partially through the substrate core such that a width extension of the heating element essentially coincides with the major axis of symmetry and a thickness extension of the heating element essentially coincides with the minor axis of symmetry.

9. The article according to claim 8, wherein the strip-shaped heating element is a resistive heating element or a susceptor element.

10. An aerosol-generating system comprising a rod-shaped aerosol-generating article according to claim 1, and an electrically heated aerosol-generating device comprising a receiving chamber for at least partially accommodating the aerosol-generating article.

* * * * *